United States Patent [19]

Stille

[11] 4,393,240
[45] Jul. 12, 1983

[54] OPTICALLY ACTIVE PHOSPHINES

[76] Inventor: John K. Stille, c/o Polymer Sciences Corporation, 330 Madison Ave., New York, N.Y. 10017

[21] Appl. No.: 280,220

[22] Filed: Jul. 6, 1981

[51] Int. Cl.³ .......................... C07F 9/50; C07F 15/00
[52] U.S. Cl. .................................. 568/13; 260/429 R; 560/142
[58] Field of Search ........................ 260/429 R; 568/13

[56] References Cited

U.S. PATENT DOCUMENTS

| | | | |
|---|---|---|---|
| 3,939,188 | 2/1976 | McVicker | 260/429 R |
| 3,949,000 | 4/1976 | Violet | 260/429 R X |
| 4,008,281 | 2/1977 | Knowles et al. | 260/429 R X |
| 4,201,728 | 5/1980 | Hughes | 260/429 R X |

OTHER PUBLICATIONS

King et al., J. Org. Chem. V44, pp. 1729–1731 (1979).
Halpern et al., J.A.C.S. V99, pp. 8055–8057 (1977).
Kagan et al., J.A.C.S. V94, pp. 6429–6433 (1972).
Detellier et al., J.A.C.S. V100, pp. 7556–7561 (1978).

*Primary Examiner*—Helen M. S. Sneed
*Attorney, Agent, or Firm*—Pennie & Edmonds

[57] ABSTRACT

The compounds (R)-1,2-bis(diphenylphosphino)-3-benzyloxypropane and (R)-1-tert-butoxy-2,3-bis(diphenylphosphino)propane are precursors to new rhodium-based asymmetric reaction catalysts having the formula:

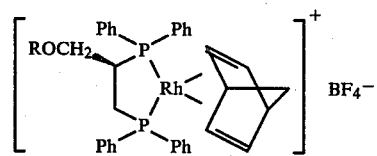

wherein R is benzyl or tert-butyl.

6 Claims, No Drawings

OPTICALLY ACTIVE PHOSPHINES

DESCRIPTION

1. Technical Field

This invention relates to the preparation of optically active chemical compounds. More particularly, it relates to the synthesis of optically active organic compounds by asymmetric chemical transformation, using homogeneous transition metal catalysis.

2. Background Art

Chemicals of biological significance have become increasingly important in industrial as well as in university laboratories. This is particularly true in the pharmaceutical field where, for example, synthetic analogs of natural products have become the subject of great deal of current research and development.

Compounds of pharmaceutical value frequently contain a center of molecular asymmetry, thereby possessing optical activity. Since many of these optically active products are often found to have much higher biological activities than either their racemic or antipodal counterparts, considerable efforts have been devoted to obtaining such optically active end-products on a commercial scale.

Concurrent with the growing interest in asymmetric compounds, the need for reliable and efficient sources of appropriate starting materials, reagents and intermediates has also grown. The common methods for obtaining optically active products can be grouped into three general categories: (1) direct resolution of racemic product mixtures using resolving agents such as certain enzymes; (2) optical resolution by crystallization of diasteriomeric mixtures; and (3) the synthesis of optically active products using optically pure (i.e., chiral) precursors (starting materials, intermediates) reagents and/or catalysts. Traditional methods in these categories are typically tedious, expensive and often unreliable. However, an example of the third category which does not suffer these drawbacks is the use of transition metalbased catalysts having chiral ligands for asymmetric hydrogenations and formylations of achiral substrates for the synthesis, e.g., of chiral amino acids in homogeneous media.

Of the methods for synthesizing optically active organic compounds, the generation of an optically active product from a prochiral reactant by use of an optically active catalyst or enzyme has several advantages, the most important of which is that either an available, naturally occurring catalyst or enzyme is utilized, or resolution is achieved with the catalyst instead of with the product. When resolution is carried out with the catalyst, only small quantities of resolved material are necessary, whereas product resolution often results in loss of one enantiomer and possibly the resolving agent.

Homogeneously catalyzed reactions generally occur at lower temperatures and pressures than do heterogeneous reactions, and are usually more enantiomerselective. Because of this, homogeneous catalysis has become a valuable tool in the art of asymmetric synthesis from prochiral reactants using optically active ligands coordinatively bound to the transition metal moiety of the catalyst. Thus, medically important amino acids of commercial significance, such as L-Dopa, for example, can be synthesized in high optical purity and yields by asymmetric hydrogenation of the prochiral alpha-N-acylaminoacrylic acids with an optically active Wilkinson type catalyst. A recent review of the state-of-the-art on asymmetric hydrogenation of prochiral unsaturated compounds to yield amino acid derivatives is given in R. E. Merrill, *Chemtech*, 11, 118 (1981).

The rhodium-based catalyst is chiral by virtue of the chirality of the phosphine ligand coordinated to it. Thus, the problem of synthesizing a suitable catalyst that will effect the asymmetric hydrogenation reaction in high enantiomeric excess ("EE") (i.e., the percentage of the predominant enantiomer minus the percentage of the less prevalent enantiomer) centers around the synthesis of a suitable optically active phosphine.

Two examples of heretofore known phosphines that combine with rhodium to give coordination complexes capable of catalyzing the hydrogenation of prochiral alpha-N-acylaminoacrylic acid derivatives in high EE ($\geq 90\%$) are (R)-1,2-bis(diphenylphosphino)propane (known trivially as "PROPHOS") and (R)-1,2-bis(diphenylphosphino)butane (known trivially as "CHIRAPHOS"). However, these and other phosphines, which are described in the aforementioned Merrill article, suffer a drawback in that their syntheses are complicated and the products themselves are therefore quite expensive.

In view of the foregoing, there is a considerable need for and incentive to provide new and more readily obtainable catalysts and more facile procedures for achieving convenient, economical and reliable asymmetric chemical transformations to produce commercially useful optically active products.

Accordingly, it is an object of the present invention to provide new, improved and relatively inexpensive ligands to be used in forming transition metal coordination complex catalysts for asymmetric chemical transformations.

Another object is to provide facile and convenient methods for preparing new and improved ligands (e.g., from readily available starting materials) to be used in forming transition metal coordination catalysts for asymmetric chemical transformations.

Another object is to provide new, improved and relatively inexpensive transition metal coordination complex catalysts for asymmetric chemical transformations.

Another object is to provide facile and convenient methods for preparing new and improved transition metal coordination complex catalysts for asymmetric chemical transformations.

Yet another object is to provide procedures for effecting asymmetric chemical transformations to produce commercially useful optically active products using new, improved and relatively inexpensive transition metal coordination complex catalysts.

These and other objects of the invention, as well as a fuller understanding of the advantages thereof, can be had by reference to the following description and claims.

DISCLOSURE OF THE INVENTION

The foregoing objects are achieved according to the present invention by the discovery of two new optically active bidentate phosphine ligands.

One of these ligands is (R)-1,2-bis(diphenylphosphino)-3-benzyloxypropane. It is prepared according to the invention by contacting and reacting 1,2-O-ditosyl-3-O-benzyl-D-glycerol with an alkali metal (e.g., sodium, potassium) diphenylphosphine.

The other ligand is (R)-1-tert-butoxy-2,3-bis(diphenylphosphino)propane. It is prepared according to the invention by contacting and reacting (+)-1-tert-butyl-2,3-di-para-toluenesulfonyl glycerol with an alkali metal (e.g., sodium, potassium) diphenylphosphine to form an intermediate product. The latter is contacted sequentially with nickel(II) chloride and an alkali metal thiocyanate to form the complex [Ni(SCN)(bisphosphine)SCN]. The complex is reacted with an alkali metal cyanide (e.g., NaCN, KCN) to form the ligand product.

Each of the foregoing ligands, when contacted and reacted with a transition metal (e.g., rhodium) norbornadienechloride dimer and sodium tetrafluoroborate, forms a transition metal-based coordination complex catalyst having the following formula:

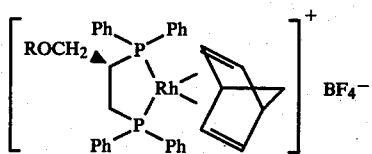

wherein R is benzyl or tertiary butyl. Such catalysts make possible certain asymmetric chemical transformations, e.g., the hydrogenation of dehydroamino acid derivatives such as alpha-N-acylaminoacrylic acids.

As indicated above, the present invention has to do with two new chiral chelating phosphines. Each of these compounds has one chiral carbon center to which one of the phosphino groups is directly bound. In another aspect of the invention, the two phosphines are synthesized from naturally occurring D-mannitol and both produce the naturally occurring L-amino acids when utilized as catalysts for the hydrogenation of alpha-N-acylaminoacrylic acid derivatives. Further, the phosphines are readily convertable to other phosphine derivatives.

The synthetic route to one of the phosphines of the invention, (R)-1,2-bis(diphenylphosphino)-3-benzyloxypropane, (E), is outlined in Scheme 1, below. Illustrative details of the synthesis are given in Examples 1 and 2.

Scheme 1
Synthesis of (R)-1,2-bis(diphenylphosphino)-3-benzyloxypropane from D-mannitol

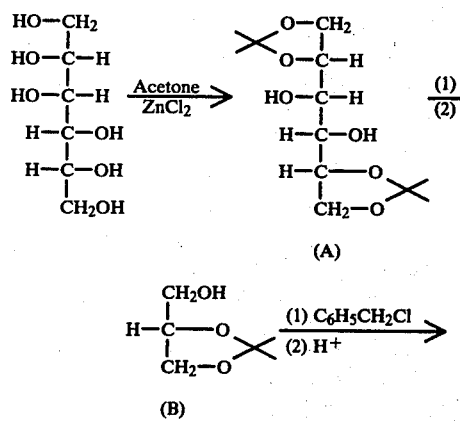

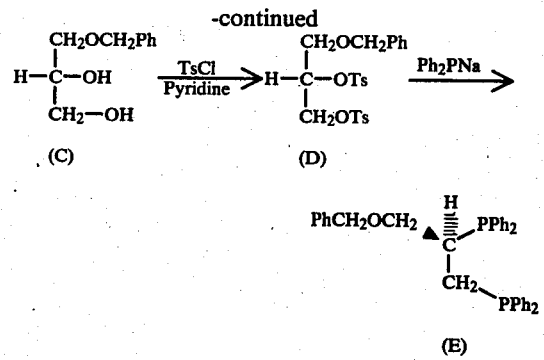

The synthetic route to the second phosphine, (R)-1-t-butoxy-2-3-bis(diphenylphosphino)propane, (K), is outlined in Scheme 2. Illustrative details of the synthetic procedure are given in Examples 3-6. This phosphine (K) can be easily converted to (R)-1,2-bis(diphenylphosphino)-propane-3-ol, (L), by acid catalyzed cleavage of the t-butyl group, as illustrated in Example 7. The phosphine (E) can also be readily converted to phosphine (L) by hydrogenolysis. Phosphine (L) can subsequently be converted to a wide variety of useful alcohol derivatives, including ethers, esters, urethanes, and the like. Thus, an important advantage of the invention is the fact that the present phosphines (E) and (K) possess sterically useful blocking groups which are sufficiently labile to certain chemical treatments to permit conversion thereof to another useful phosphine, (L).

Scheme 2
Synthesis of (R)-1-t-butoxy-2,3-bis(diphenylphosphino)propane from D-mannitol

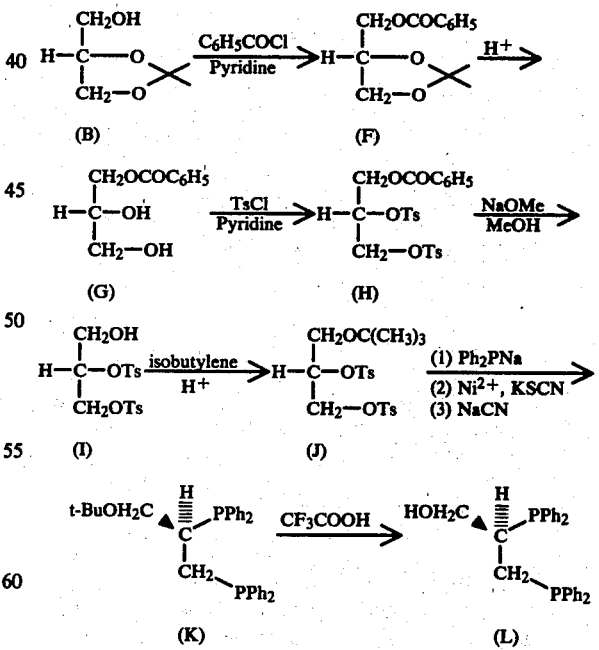

Both phosphines, (E) and (K), of this invention, can be converted to rhodium complexes, (M) and (N), respectively, as outlined in Scheme 3. Illustrative details of the procedures for synthesizing of these complexes are given in Examples 8 and 9.

Scheme 3

Representative Preparation of a Rhodium Catalyst from Optically Active Phosphines E and K

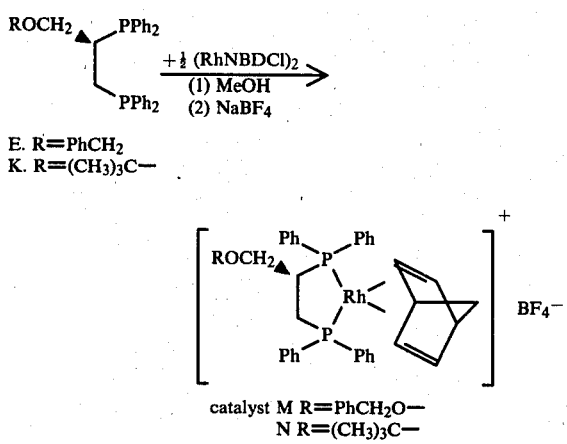

E. R=PhCH$_2$
K. R=(CH$_3$)$_3$C— catalyst M R=PhCH$_2$O—
N R=(CH$_3$)$_3$C—

Thus, compounds (E) and (K) serve as ligand precursors to rhodium-based coordination complexes (M) and (N) which are useful as catalysts for the hydrogenation of prochiral alpha-N-acylamino-acrylic acid to amino acid derivatives in high optical yields. Some examples of hydrogenation reactions that can be carried out at 1 atm of hydrogen at room temperature or even lower temperature are the following:

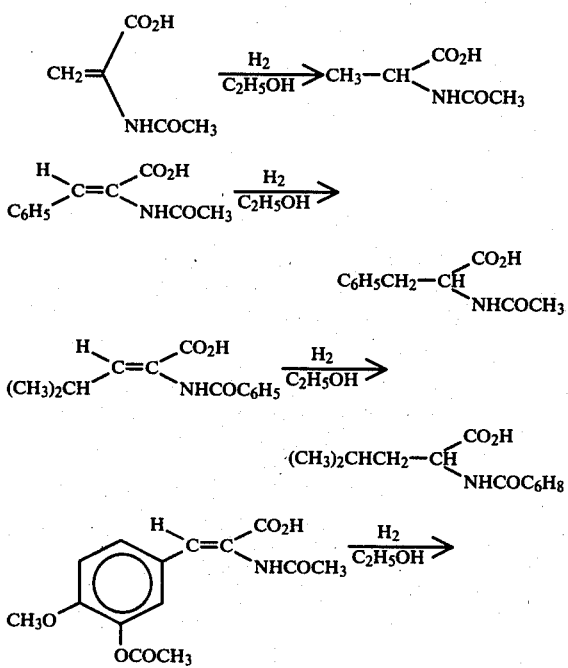

The hydrogenation reactions are conveniently carried out in alcohol solvents, and quantitative conversions to the amino acid products are achieved. Some representative optical yields obtained in the hydrogenation reactions of such substrates are given in Tables 1 and 2 for catalysts (M) and (N), respectively. The configuration of the amino acid products is S or that which is naturally occurring. The hydrogenation procedure is given in Example 10.

BEST MODE OF CARRYING OUT THE INVENTION

The following examples are intended to illustrate without limitation the present invention and its advantages.

EXAMPLE 1

Synthesis of 1,2-O-Ditosyl-3-O-benzyl-D-glycerol (See Formula (D) in Scheme 1)

The synthesis of 1,2:5,6-diacetone-D-mannitol (see Formula (A) in Scheme 1) is accomplished by the method of E. Baer, *Biochem. Prep.*, 2, 31 (1952); the compound is recrystallized from n-butyl ether and has a m.p. of 120°–121° C. Next, 1,2-O-isopropylidene-D-glycerol (see Formula (B) in Scheme 1) is obtained from 1,2:5,6-diacetone-D-mannitol by the method of J. LeCaq and C. E. Ballou, *Biochemistry*, 3, 976 (1964) and has an $[\alpha]_D$ of +14.6 (neat). Then, 3-O-benzyl-Sn-glycerol (see Formula (C) in Scheme 1) is prepared from 1,2-O-isopropylidene-D-glycerol by the method of B. T. Golding and P. V. Ioannou, *Synthesis*, 423 (1977).

To a solution of 5 g (27.5 mmole) of diol (C) in 20 ml of dry pyridine cooled in an ice bath are added 12 g (62.82 mmol) of recrystallized tosylchloride dissolved in 30 ml of dry pyridine. The solution is stored in a refrigerator for 6 days. Water (10 ml) is added and the mixture is stirred for 10 minutes. The solution is then poured into 500 ml of cold water with stirring. The precipitated product is dissolved in chloroform and the aqueous solution is extracted with chloroform. The combined chloroform solution is washed with cold 3 N hydrochloric acid until the wash water is acidic to litmus. The chloroform layer is then washed successively with water, 5% sodium bicarbonate solution, and finally with water. The chloroform solution is dried over anhydrous sodium sulfate. The solvent is removed under reduced pressure and the residue dried in vacuo. Recrystallization from absolute ethanol affords pure 1,2-O-ditosyl-3-O-benzyl-D-glycerol (see Formula (D) in Scheme 1), m.p. 60°–62° C. $^1$H NMR (CDCl$_3$)δ7.7–7.5 (4H, m); 7.2 (9H, m), 4.7–4.4 (1H, m); 4.3 (2H, s); 4.15 (2H, d); 2.35 (6H, s). $^{13}$C NMR (CDCl$_3$) 144.872, 144,775, 136,968, 132.688, 131.788, 131,739, 129.624, 129.526, 129.283, 127.970, 127.483, 127.143, 76.801, 72.910, 67.417, 21.352.

EXAMPLE 2

(R)-1,2-bis(diphenylphosphino)-3-benzyloxypropane (See Formula (E) in Scheme 1)

A three-necked 100 ml flask equipped with a dry ice condenser, a nitrogen inlet and a dropping funnel is cooled in an isopropanol-dry ice bath and 25 ml of ammonia are condensed into it. To the liquid ammonia is added 0.575 g (25.0 g atom) of sodium, and the solution is stirred for 10 minutes. To the sodium in liquid ammonia solution 4.6 g (25.0 mmol) of diphenylphosphine dissolved in 20 ml of dry tetrahydrofuran are added dropwise over a period of about 10 minutes.

When the addition is complete, the dry ice bath is removed and the ammonia is allowed to vaporize. When the solution attains room temperature, 5.4 g (11.02 mmol) of 1,2-O-ditosyl-3-O-benzyl-D-glycerol (see Formula (D) in Scheme 1) dissolved in 30 ml of dry tetrahydrofuran is added to it dropwise. When the addition is completed, the reaction mixture is stirred at ambient or room temperature overnight and then at 40°–45° C. (bath temperature) for 4 hours. The yellow reaction mixture is then centrifuged, and the clear yellow liquid thus obtained is concentrated in vacuo, dried overnight and recrystallized from absolute ethanol to yield 2.4 g (4.63 mmol, 42%) of (R)-1,2-bis(diphenylphosphino)-3-benzyloxypropane (see Formula (E) in Scheme 1) as white crystals, m.p. 88° C. $[\alpha]_D$+71.5° C. (C, 1, CHCl$_3$). $^1$H NMR (CDCL$_3$) δ7.1 (m. ArH); 4.35 (s, C$_6$H$_5$CH$_2$); 3.9 (m, 1H); 3.4 (m, 1H); 2.5 (m, 2H); 2.15 (m, 1H). $^{31}$P NMR (CDCl$_3$, sub ref. H$_3$PO$_4$) 6.264 (d, J=26.5 Hz); 18.996 (d, J=26.5 Hz). $^{13}$C NMR (CDCL$_3$)δ138.819, 138.282, 138.235, 137.847, 137.629, 136.726, 136.679, 136.049, 135.465, 133.668, 133.543, 133.279, 132.866, 132.765, 132.158, 131.450, 128.727, 128.680, 128.633, 128.439, 128.268, 128.143, 128.073, 127.949, 127.878, 127.731, 127.322, 127.198, 127.054, 126.882, 126.711, 72.658 (s), 69.351 (t), 34.772 (t), 27.866 (t).

EXAMPLE 3

(−)-1-Benzoyl-2,3-di-p-toluenesulfonyl glycerol (See Formula (H) in Scheme 2)

The compound (+)3-benzoyl-1,2-isopropylidene glycerol (see Formula (F) in Scheme 2) is obtained from 1,2-O-isopropylidene-D-glycerol (see Formula (B) in Scheme 1) by the method of J. LeCaq and C. E. Ballou, *Biochemistry*, 3, 976 (1974) and has an $[\alpha]_D$ of +14.4 (neat). Next, (−)-1-benzoyl glycerol (see Formula (G) in Scheme 2) is prepared from (+)-3-benzoyl-1,2-isopropylidene glycerol by the method of E. Baer, I. B. Cushing and H. O. L. Fischer, *Can. J. Research*, 21B, 119 (1943) and has an $[\alpha]_D$−15 (C, 10, in pyridine).

To a solution of 35.5 g (181 mmol) of (−)-1-benzoyl glycerol (G) in 250 ml of dry pyridine at 0° C. is added 83 g (433 mmol) of p-toluenesulfonyl chloride. The mixture is stirred at 0° C. for 15 minutes and then stored in a refrigerator for 144 hours. After cooling the reaction mixture to 0° C., 10 ml of water are added, the mixture is stirred for 10 minutes, and then poured into excess water. The aqueous solution is separated from the gummy product, and extracted with chloroform. The gummy residue is dissolved in chloroform and the combined chloroform solution is washed sequentially with 3 N hydrochloric acid, water, 5% sodium bicarbonate solution, and water. The chloroform solution is dried over Na$_2$SO$_4$ and concentrated under reduced pressure to obtain a solid which, upon recrystallization from absolute ethanol, gives 65.5 g (130 mmol, 72%) of (−)-1-benzoyl-2,3-di-p-toluenesulfonyl glycerol (see Formula (H) in Scheme 2), m.p. 105°–106° C. $[\alpha]_D^{2°}$−22.7 (c, 5.92, CHCl$_3$). $^1$H NMR (CDCl$_3$) δ8–7 (m, 13H); 4.9 (m, 1H); 4.45 (d, 2H, J=6 Hz); 4.35 (d, 2H, J=5 Hz); 2.42 (s, 3H); 2.38 (s, 3H). $^{13}$C NMR (CDCl$_3$) 165.162, 145.136, 133.108, 132.466, 131.649, 129.430, 128.671, 128.087, 127.678, 75.306, 66.899, 61.994, 21.591 ppm.

EXAMPLE 4

(−)1,2-Di-p-toluenesulfonyl glycerol (See Formula (I) in Scheme 2)

To a slurry of 20 g (39.7 mmol) of (−)-1-benzoyl-2,3-di-p-toluenesulfonyl glycerol (see Formula (H) in Scheme 2) in 250 ml of dry methanol, cooled in an ice bath, are added 250 mg (10.87 mmol) of sodium under nitrogen atmosphere. The mixture is stirred at 0° C. for 3 hours, during which time the solution becomes homogeneous, indicating the completion of hydrolysis. The solution is neutralized by means of an ion exchange resin (Dowex 50 W−x8, H+ form), the resin is filtered, solvent is removed on a rotary evaporator, and the product dried in vacuo. It is redissolved in 200 ml of chloroform, washed with water, dried over Na$_2$SO$_4$ and concentrated to yield 14.0 g (35.0 mmol, 88%) of (−)-1,2-di-p-toluenesulfonyl glycerol (see Formula (I) in Scheme 2) in the form of a viscous oil. $^1$H NMR (CDCl$_3$)δ7.8 (m, 4H); 7.4 (m, 4H); 4.7 (m, 1H); 4.2 (d, 2H, J=5 Hz); 3.75 (t, 2H, J=6 Hz); 2.7 (t, 1H, OH); 2.5 (s, 6H). $[\alpha]_D$=−18.53 (c, 66, CHCl$_3$).

EXAMPLE 5

(+)-1-t-Butyl-2,3-di-p-toluenesulfonyl glycerol (See Formula (J) in Scheme 2)

A solution of 13.8 g (34.5 mmol) of (−)-1,2-di-p-toluene-sulfonyl glycerol (see Formula (I) in Scheme 2) in 100 ml of dry methylenechloride is added to 100 ml of liquid isobutylene taken in a pressure bottle at −78° C. Concentrated sulfuric acid (0.2 ml) is added to the above reaction mixture, the contents are stirred, and the mixture is then allowed to warm to room temperature and stirred for 16 hours. The pressure is gradually released, and the solution is neutralized with aqueous sodium bicarbonate solution. The organic layer is separated, washed with water, and dried over Na$_2$SO$_4$. The solvent is removed on a rotary evaporator and the crude product is dried under reduced pressure. Recrystallization from absolute ethanol affords white crystals of (+)-t-butyl-2,3-di-p-toluenesulfonyl glycerol (see Formula (J) in Scheme 2), m.p. 70°–71° C. $[\alpha]_D^2$+3.44 (c, 5.9, CHCl$_3$). $^1$H NMR (CDCl$_3$)δ7.8 (m, 4H); 7.3 (m, 4H); 4.5 (m, 1H); 4.15 (d, 2H); 3.35 (d, 2H); 2.45 (s, 6H); 1.1 (s, 9H).

EXAMPLE 6

(R)-1-t-Butoxy-2,3-bis(diphenylphosphino)propane (See Formula (K) in Scheme 2)

Liquid ammonia (100 ml) is condensed at −70° C. into a 250 ml three-necked flask, equipped with a magnetic stirbar, dropping funnel, Dewar condenser and a nitrogen inlet. To this are added 1.31 g (57.0 mmol) of sodium and the system is stirred for 10 minutes. To the resulting dark blue solution of sodium in liquid ammonia are added 10.6 g (57.0 mmol) of diphenylphosphine dissolved in 50 ml of dry THF. This addition is carried out dropwise over a period of 45 minutes. By the time all the diphenylphosphine has been added, the color of the solution becomes orange. Excess ammonia is allowed to evaporate from the clear orange solution under a stream of argon. When the solution attains room temperature, a solution of 13.0 g (28.5 mmol) of (+)-1-t-butyl-2,3-di-p-toluenesulfonyl glycerol (see Formula (J) in Scheme 2) in 50 ml of dry THF is added dropwise over a period of 30 minutes. The mixture is allowed to remain at room temperature for 18 hours with stirring. The precipitated sodium p-toluenesulfonate is removed by centrifugation. The clear THF solution is concentrated under reduced pressure to give the impure phosphine.

The crude phosphine is redissolved in 50 ml of absolute ethanol under argon atmosphere and a solution of 7 g of $NiCl_2 \cdot 6H_2O$ in 25 ml of absolute ethanol is added to it and the contents stirred for 15 minutes. This was followed by addition of a solution of 7 g of potassium thiocyanate in 25 ml of 90% aqueous ethanol. The complex [Ni(SCN)(bisphosphine)SCN] separates upon stirring over a period of 18 hours in the form of a yellow powder which is collected by filtration and washed thoroughly with absolute ethanol and ether.

To free the phosphine from the above-described nickel complex, the complex is suspended in 50 ml of dichloromethane and a solution of 18 g of sodium cyanide in 50 ml of water is added. The mixture is stirred vigorously for 1 hour during which time all of the nickel complex is dissolved and the dark red color of the organic layer changes to pale yellow. The organic layer is separated, washed with water and concentrated under reduced pressure to yield a light yellow phosphine. Recrystallization of this slightly impure phosphine from absolute ethanol gives 2 g of white needle-like crystals of (R)-1-t-butoxy-2,3-bis(diphenylphosphino)propane (see Formula (K) in Scheme 2), m.p. 77°–78° C. $[\alpha]_D + 91$ (C, 1, $CHCl_3$). $^1H$ NMR ($CDCl_3$)δ7.1 (m, 20H); 3.5 (m, 2H); 2.3 (m, 3H); 1.1 (s, 9H). $^{31}P$ NMR ($CDCl_3$, sub. ref. $H_3PO_4$); −5.412 (d, J−25 Hz); −19.077 (d, J=25 Hz) ppm.

EXAMPLE 7

(R)-1,2-Bis(diphenylphosphino)propane-3-ol (See Formula (L) in Scheme 2)

A solution of 0.2 g of (R)-1-t-butoxy-2,3-bis-(diphenylphosphino)propane (see Example 6) in 25 ml of anhydrous trifluoroacetic acid under argon atmosphere is stirred at room temperature for 14 hours. The trifluoroacetic acid is removed under reduced pressure. The residue is dissolved in 20 ml of dichloromethane, and washed with 5% sodium bicarbonate solution and then with water. The solvent is removed under reduced pressure and the residue is dried to yield 0.16 g of (R)-1,2-bis-(diphenylphosphino)propane-3-ol (see Formula (L) of Scheme 2) in the form of a sticky solid.

EXAMPLE 8

Synthesis of the Rhodium Complex (See Formula (M) in Scheme 3)

The catalyst is prepared and used under an inert atmosphere. Extreme care must be taken to exclude air from the solvents.

To a solution of 42.7 mg (0.0925 mmol) of the dimer of rhodium norbornadienechloride $(RhNBDCl)_2$ in 3 ml of methanol are added 105.0 mg (0.203 mmol) of (R)-1,2-bis(diphenylphosphino)-3-benzyloxypropane (see Formula (E) in Scheme 1) of Example 2. The reaction mixture is stirred at room temperature for 2 hours. To this is added a solution of 1.95 g of sodium tetrafluoroborate in 18 ml of water. The rhodium complex (see Formula (M) in Scheme 3) is precipitated as a yellow, cheesy solid which is collected by filtration, washed with water and dried. The complex is used for the asymmetric hydrogenation of various alpha-acylaminoacrylic acid derivatives. $^{31}P$ ($CH_3OD$, sub. ref. $H_3PO_4$); 60.22 (dd, $J_{Rh-P}$, 157 Hz, $J_{P-P}$, 32 Hz); 46.41 (dd, $J_{Rh-P}$, 155 Hz, $J_{P-P}$, 32 Hz).

EXAMPLE 9

Synthesis Of The Rhodium Complex (See Formula (N) In Scheme 3)

A solution of 12 mg (0.020 mmol) of (R)-1-t-butoxy-2,3-bis(diphenylphosphino)propane (see Formula (K) in Scheme 2) and 4.6 mg (0.010 mmol) of $(RhNBDCl)_2$ in 1 ml of methanol is stirred at room temperature for 1 hour. The catalyst is precipitated as the cationic complex by the addition of 0.15 g (1.4 mmol) of sodium borofluorate in 3 ml of water. The precipitated catalyst is collected by filtration, washed with water and dried.

EXAMPLE 10

General Hydrogenation Procedure (See Tables 1 and 2)

Ethanol and methanol are distilled from magnesium ethoxide and methoxide, respectively, and then deoxygenated by repeatedly pumping and filling with argon. The substrate (0.3–0.5 g) is weighed into a two-necked flask fitted with a gas inlet and a serum cap. This system is degassed by evacuating and filling with argon several times. The catalyst precursor (e.g., the rhodium complex of formula (M) or (N) in Scheme 3; Examples 8 and 9) dissolved in 10–15 ml of the solvent is transferred to the flask containing the substrate via a needle stock. The solution is vigorously stirred under one atmosphere of hydrogen pressure for a period of 2–24 hours. After this period of time, the solvent is removed and the product is separated from the catalyst either by dissolving the product in water and filtering to remove the catalyst (alanine and L-DOPA derivatives) or by dissolving the product in 0.5 N NaOH solution, filtering to remove the catalyst, acidifying the aqueous filtrate, and extracting the latter with ether. The conversions are determined using $^1H$ NMR. Optical purity is determined by checking the rotation on a polarimeter. The results of these hydrogenations are listed in Tables 1 and 2.

TABLE 1

Asymmetric Hydrogenations Using the Catalyst Precursor M

| Substrate | Product | Solvent | op.y. (config.) |
|---|---|---|---|
| H\\_/COOH  / \\ H   NHCOCH₃ | N—acetylalanine | EtOH | 91 (S) |
| H\\_/COOH  / \\    NHCOPh | N—benzoyl-lencine | EtOH MeOH | 78 (S) 74 (S) |
| H\\_/COOH  / \\ Ph  NHCOCH₃ | N—acetylphenyl-alanine | EtOH | 87 (S) |
| H\\_/COOH  / \\ Ph  NHCOPh | N—benzoyl-lencine | MeOH | 72 (S) |

TABLE 1-continued

Asymmetric Hydrogenations Using the Catalyst Precursor M

| Substrate | Product | Solvent | op.y. (config.) |
|---|---|---|---|
| 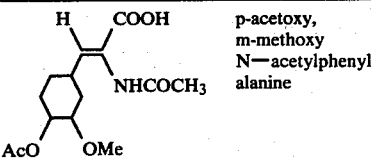 | p-acetoxy, m-methoxy N—acetylphenyl-alanine | EtOH | 91 (S) |

TABLE 2

Asymmetric Hydrogenations Using Catalyst Precursor N

| Substrate | Product | Optical Yield |
|---|---|---|
| COOH<br>=<<br>NHCOCH$_3$ | N—acetylalanine | 92 |
| H COOH<br>⟩=⟨<br>NHCOPh | N—benzoylleucine | 88 |
| H COOH<br>⟩=⟨<br>Ph NHCOCH$_3$ | N—acetylphenylalanine | 86 |

All hydrogenations were carried in ethanol as the solvent. The predominant isomer had the S configuration.

The foregoing examples are intended to illustrate the features and advantages of the preferred embodiments of the present invention. It is understood, of course, that changes and variations can be made in the herein disclosed invention without departing from the scope thereof as defined in the following claims.

Having disclosed my invention in the foregoing description, what I claim as new and desired to secure by Letters Patent is:

1. (R)-1,2-bis(diphenylphosphino)-3-benzyloxypropane.

2. A process for producing (R)-1,2-bis(diphenylphosphino)-3-benzyloxypropane, comprising chemically reacting 1,2-O-ditosyl-3-O-benzyl-D-glycerol with sodium diphenylphosphine.

3. (R)-1-tert-butoxy-2,3-bis(diphenylphosphino)propane.

4. A process for producing (R)-1-tert-butoxy-2,3-bis(diphenylphosphino)propane, comprising chemically reacting (+)-1-tert-butyl-2,3-paratoluenesulfonyl glycerol with sodium diphenylphosphine to form an intermediate product, contacting said intermediate product sequentially with nickel(II) chloride and an alkali metal thiocyanate to form the complex [Ni(SCN)(bisphosphine)SCN], and contacting and reacting said complex with an alkali metal cyanide.

5. (R)-1,2-bis(diphenylphosphino)propane-3-ol.

6. A process for producing (R)-1,2-bis(diphenylphosphino)propane-3-ol, comprising chemically reacting (R)-1-tert-butoxy-2,3-bis(diphenylphosphino)propane with anhydrous trifluoroacetic acid to effect acid-catalyzed cleavage of the tert-butyl group.

* * * * *

UNITED STATES PATENT AND TRADEMARK OFFICE
CERTIFICATE OF CORRECTION

PATENT NO. : 4,393,240
DATED : July 12, 1983
INVENTOR(S) : John K. Stille

It is certified that error appears in the above-identified patent and that said Letters Patent are hereby corrected as shown below:

Column 6, line 51, "$^3C$ NMR" should read --$^{13}C$ NMR--.

Table 1, 5th drawing, "" should read ----.

Signed and Sealed this

Twentieth Day of September 1983

[SEAL]

Attest:

GERALD J. MOSSINGHOFF

Attesting Officer  Commissioner of Patents and Trademarks